United States Patent [19]

Lippmann et al.

[11] 4,070,482

[45] Jan. 24, 1978

[54] PROSTAGLANDIN ANTAGONISTS

[75] Inventors: Wilbur Lippmann, Montreal; Jehan F. Bagli, Kirkland, both of Canada

[73] Assignee: Ayerst, McKenna & Harrison Ltd., Montreal, Canada

[21] Appl. No.: 735,929

[22] Filed: Oct. 27, 1976

Related U.S. Application Data

[62] Division of Ser. No. 545,664, Jan. 2, 1975, Pat. No. 4,004,027.

[51] Int. Cl.$^2$ .................. C07C 177/00; A61K 31/215; A61K 31/19
[52] U.S. Cl. ............................. 424/317; 260/345.7 P; 260/345.8 P; 260/514 D; 424/305; 560/121; 560/231

[58] Field of Search ....... 260/468 D, 514 D, 514 CA; 424/305, 317

[56] References Cited

U.S. PATENT DOCUMENTS

| B 491,711 | 3/1976 | Kao et al. | 260/240 |
|---|---|---|---|
| 3,922,302 | 11/1975 | Strike | 260/514 |

Primary Examiner—Robert Gerstl
Attorney, Agent, or Firm—Stephen Venetianer

[57] ABSTRACT 2-(1-Hydroxy-2-octynyl)- and 2-(3-hydroxy-1-octynyl)-5-oxocyclopentaneheptanoic acids, their salts and their corresponding lower alkyl esters are disclosed. The compounds inhibit the actions of prostaglandins. Methods for their preparation and use are given.

5 Claims, No Drawings

PROSTAGLANDIN ANTAGONISTS

This is a continuation division of application serial no. 545,664 filed Jan. 2, 1975 now U.S. Pat. No. 4004027.

BACKGROUND OF THE INVENTION a. Field of the Invention

This invention relates to prostanoic acid derivatives capable of inhibiting the actions of prostaglandins, to processes for preparing these derivatives and to methods for using said derivatives.

b. Prior Art

The number of substances which inhibit prostaglandin actions is relatively small. See, for example, the review by J. H. Sanner, Arch. Intern. Med., 133, 133 (1974). Chemically the most interesting of the substances fall into three catagories: dibenzoxazepines, phosphorylated polymers of phloretin and 7-oxaprostaglandin analogs. Apparently, only one report has appeared describing prostaglandin inhibiting properties for compounds having the total carbon skeleton of a prostanoic acid. In this instance, the antiprostaglandin effect was a desensitization of rat uterus and gerbil colon tissue to prostaglandin $E_2$ by the prostaglandin analogs 11,15-epi-prostaglandin $E_2$ and ent-11,15-epi-prostaglandin $E_2$, E. J. Corey, et al., J. Org. Chem., 37, 3043 (1972); on the other hand, these prostaglandin analogs produced a prostaglandin-like effect on the tissues indicating mixed agonist and antagonist properties for the analogs.

In accordance with the present invention a series of compounds having the prostanoic acid carbon skeleton are disclosed; the compounds inhibit the actions of prostaglandins in the manner of a specific prostaglandin antagonist in that they do not exhibit appreciable agonist properties.

One of the compounds contained herein, i.e. 2-(3-hydroxy-loctynyl)-5-oxocyclopentaneheptanoic acid, and its lower alkyl esters (formula 1 in which A is —C≡C—CHOH— and $R^1$ is hydrogen or lower alkyl) have been disclosed before, see West German Offenlegungsschrift 2,318,595, published 1973; however, the activities reported therein for these compounds were prostaglandin-like in nature.

SUMMARY OF THE INVENTION

The compounds of this invention are represented by general formula 1

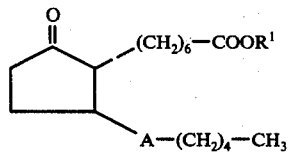

in which A is an organic radical selected from the group consisting of —CHOH-C≡C— and —C≡C-CHOH- and $R^1$ is hydrogen or lower alkyl.

The preferred compounds of this invention are those of formula 1 in which A is —CHOH—C≡C— and $R^1$ is hydrogen or lower alkyl.

The compounds of formula 1 in which A is —CHOH—C≡C— are prepared by a process illustrated in the following flow diagram:

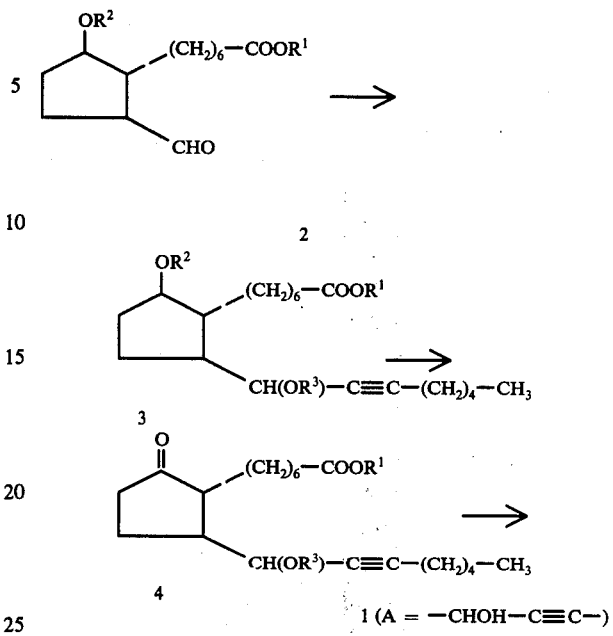

With reference to the preceding flow diagram, the process comprises condensing a compound of formula 2 in which $R^1$ is hydrogen or lower alkyl and $R^2$ is a hydroxy protective group with the lithium derivative of 1-heptyne to obtain the corresponding dihydroxyprostanoic acid derivative of formula 3 in which $R^1$ is hydrogen or lower alkyl, $R^2$ is a hydroxy protective group and $R^3$ is hydrogen. The latter compound is subjected to acylating conditions whereby the free hydroxy group on the side chain is acylated to yield the corresponding compound of formula 3 in which $R^1$ is hydrogen or lower alkyl, $R^2$ is a hydroxy protective group and $R^3$ is lower alkanoyl. Reacting the latter compound under conditions known to be effective for removing hydroxy protective groups, preferentially removes the protective group of the ringpositioned hydroxyl, transforming the compound to the corresponding compound of formula 3 in which $R^1$ is hydrogen or lower alkyl, $R^2$ is hydrogen and $R^3$ is a lower alkanoyl. Subsequent reaction of the last named compound with an oxidizing agent capable of converting a hydroxy function to the corresponding keto function gives the corresponding ketone of formula 4 in which $R^1$ is hydrogen or lower alkyl and $R^3$ is lower alkanoyl. Hydrolysis of the latter compound with a base in the presence of water gives the corresponding compound of formula 1 in which A is —CHOH-C≡C- and $R^1$ is hydrogen. If desired the latter compound is esterified to give the corresponding compound of formula 1 in which $R^1$ is lower alkyl.

The compounds of formula 1 in which A is —C≡C-CHOH— are prepared by a process illustrated in the following flow diagram:

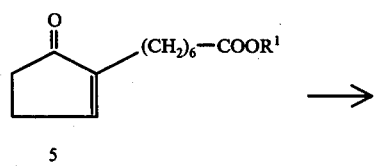

-continued

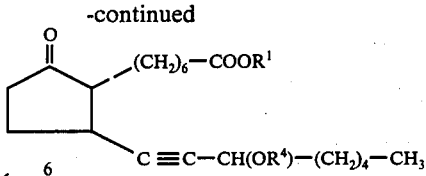

1 (A = —C≡C—CHOH—)

with reference to the above flow diagram the compound of formula 5 in which $R^1$ is hydrogen or lower alkyl is condensed with an alane derivative of the compound of formula HC≡C-CH(OR$^4$)—(CH$_2$)$_4$-CH$_3$ in which $R^4$ is a hydroxy protective group to afford the corresponding hydroxyoxoprostanoic acid derivative of formula 6 in which $R^1$ is hydrogen or lower alkyl and $R^4$ is a hydroxy protective group; the alane derivative being generated in situ from the corresponding lithium derivative and aluminum chloride. Treatment of the latter compound under conditions known to be effective for removing hydroxy protective groups gives the corresponding compound of formula 1 in which A is —C≡C-CHOH— and $R^1$ is hydrogen or lower alkyl. If desired the latter compound of formula 1 in which $R^1$ is lower alkyl is hydrolyzed with a base in the presence of water to give the corresponding compound of formula 1 in which $R^1$ is hydrogen.

According to a further aspect of this invention a method for relieving a complication from abnormally increased physiological availability of prostaglandins in a host is comprised of administering a complication alleviating dose of a compound of formula 1 to said host.

DETAILS OF THE INVENTION

The numbering system applied to the compound of this invention, as used hereinafter, refers to the ω-cyclopentyl(lower)alkanoic acid nucleus.

A feature of this invention is that the process described herein leads to the compounds of formula 1 in which the two side chains are in the trans configuration characteristic for the natural prostaglandins.

Notwithstanding the preceding considerations the compounds of this invention having more than one asymmetric carbon atoms can exist in the form of various stereochemical isomers. More specifically, the compounds are produced as a mixture of racemates. These mixtures can be separated into pure racemates at appropriate stages by methods well known in the art. If desired, the racemates can be resolved into enantiomorphs also by known methods. It is to be understood that such racemates and enantiomorphs are included within the scope of this invention.

Furthermore, it is to be understood that the pictorial representations used herein illustrating the compounds of this invention, are to be construed as including such racemates and enantiomorphs. For example, in formula 1 the dotted line joining the acid side chain to the cyclopentane ring and the solid line joining the side chain bearing the hydroxy group are used for the purpose of illustrating the trans relationship of these two side chains and should not be construed as limiting the compounds to one enantiomorph but rather as including all possible enantiomorphs having this trans relationship.

Also included within this invention are the pharmaceutically acceptable salts of the acids of formula 1 in which $R^1$ is hydrogen. The acids are transformed in excellent yield into the corresponding pharmaceutically acceptable salts by neutralization of said latter compounds with the appropriate inorganic or organic base. The relative stability of the acid facilitates this transformation. The salts possess the same activities as the parent acid compounds when administered to animals and may be utilized in the same manner. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines: lower mono-, di- and trialkylamines, the alkyl radicals of which contain up to 3 carbon atoms, such as methylamine, dimethylamine, trimethylamine, ethylamine, di- and triethylamine, methylethylamine, and the like; mono-, di- and trialkanolamines, the alkanol radicals of which contain up to 3 carbon atoms, such as mono-, di- and triethanolamine; alkylene-diamines which contain up to 6 carbon atoms, such as hexamethylenediamine; cyclic saturated or unsaturated bases containing up to 6 carbon atoms, such as pyrrolidine, piperidine, morpholine, piperazine and their N-alkyl and N-hydroxyalkyl derivatives, such as N-methyl-morpholine and N-(2-hydroxyethyl)-piperidine, as well as pyridine. Furthermore, there may be mentioned the corresponding quanternary salts, such as the tetraalkyl (for example tetramethyl), alkyl-alkanol (for example methyl-triethanol and trimethyl-monoethanol) and cyclic ammonium salts, for example the N-methyl-pyridinium, N-methyl-N-(2-hydroxyethyl)-pyrrolidinium, N,N-dimethylmorpholinium, N-methyl-N-(2-hydroxyethyl)-morpholinium, N,N-dimethyl-piperidinium and N-methyl-N-(2-hydroxyethyl)piperidinium salts, which are characterized by an especially good water-solubility. In principle, however, there can be used all ammonium salts which are physiologically compatible.

The transformations to the salts can be carried out by a variety of methods known in the art. For example, in the case of the inorganic salts, it is preferred to dissolve the selected acid in water containing at least an equivalent amount of a hydroxide, carbonate, or bicarbonate corresponding to the inorganic salt desired. Advantageously, the reaction is performed in an inert organic solvent, for example, methanol, ethanol, dioxane, and the like. For example, such use of sodium hydroxide, sodium carbonate or sodium bicarbonate gives a solution of the sodium salt. Evaporation of the water or addition of a water-miscible solvent of moderate polarity, for example, a lower alkanol or a lower alkanone gives the solid inorganic salt if that form is desired.

To produce an amine salt, the selected acid is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or diethyl ether or by evaporation. If the amine is relatively volatile, any excess can easily be removed by evaporation. It is preferred to use equivalent amounts of the less volatile amines.

Salts wherein the cation is quaternary ammonium are produced by mixing the selected acid with an equivalent amount of the corresponding quaternary ammonium hydroxide in water solution, followed by evaporation of the water.

The term "lower alkyl" as used herein contemplates straight chain alkyl groups containing from one to three carbon atoms and includes methyl, ethyl and propyl.

The term "lower alkanoyl" as used herein contemplates straight chain alkanoyl radicals containing from two to three carbon atoms and includes acetyl and propionyl.

The term "hydroxy protective group" as used herein contemplates acid liable groups suitable for protecting a hydroxy and excludes lower alkanoyl; a preferred hydroxy protective group is tetrahydropyran-2-yl (THP). Examples of other suitable protective groups include tri(lower)alkylsilyl, for instance trimethylsilyl (TMS) and dimethylisopropylsilyl (DMIS), (lower)alkoxy(lower)alkyl, for instance, ethoxyethyl, methoxyisopropyl or methoxymethyl, and tert-butyl. The transformation of the hydroxyl to a protected hydroxyl is effected by treating the precursor having the hydroxy group with a reagent known to be effective for converting a hydroxy group of a known compound to a protected hydroxy group. Such reagents include an excess of dihydropyran or an acid catalyst for example, p-toluenesulfonic acid, hydrogen chloride or sulfuric acid, for the THP group; trimethylchlorosilane with hexamethyldisilazine for the TMS group; dimethylisopropylchlorosilane and diisopropyltetramethyldisilazane for the DMIS group; ethyl vinyl ether methyl isopropenyl ether in the presence of an acid catalyst, such as described above, for the ethoxyethyl and methoxyisopropyl groups, respectively; chloromethyl methyl ether in the presence of a base, for instance sodium hydride, for the methoxymethyl group; and isobutylene for the tert-butyl group. For a detailed description of various useful hydroxy protective groups, see J. F. W. McOmie, "Protective Groups in Chemistry," Plenum Publications, New York, 1973, pp. 96 – 120.

The term "under conditions known to be effective for removing hydroxy protective group" as used herein contemplates neutral (in the case of TMS and DMIS) or mildly acidic conditions in which aqueous solutions of mineral or organic acids are used as a principal component of the reaction medium, for example, 0.1 to 12 N hydrochloric acid or 30 – 90% acetic acid, at temperatures of 0°– 80° C. Further exemplified, the THP and lower(alkoxy)lower alkyl protective groups removed by treating the protective group containing compound for ten minutes to three or four hours at 20° – 60° C with aqueous acetic acid, or with p-toluenesulfonic acid or hydrochloric acid in an inert solvent in the presence of water, preferably methanol-water (9:1). The TMS group is removed by treatment with an excess of water-methanol (10:1) for 24 hours or with tetrahydrofuran-acetic acid at room temperature for one to two hours. Likewise the DMIS group is removed by the same conditions used for the removal of the TMS group. See also McOmie, cited above.

The ability of the compound of formula 1 to inhibit the actions of prostaglandins is demonstrated in pharmacological tests. A practical test for this purpose is based on the principle that prostaglandins can stimulate adenyl cyclase to produce adenosine $3^1,5^1$-monophosphate (cyclic AMP) above the basal levels in some tissues; this activity can be antagonized by certain agents which thus exhibit antiprostaglandin activity. Descriptions of this type of test appear in the literature; for example, tests designed for determining the effect of a test compound on an induced cyclic AMP accumulation in the rat anterior pituitary; see F. Labrie, et al., J. Biol. Chem., 246, 1902 (1971) and P. Borgeat, et al., Proc. Natl. Acad. Sci. U.S.A., 69, 2677 (1972).

An exemplification of this type of test for characterizing the antiprostaglandin properties of the compounds of this invention is given as follows:

Anterior pituitaries from male Sprague-Dawley rats (180-200 g) were utilized. The experiments were initiated between 8:15 – 9:15 A.M. The anterior pituitaries, from which the posterior and intermediary lobes were removed, were separated into identical halves. Three pituitary halves were used in each group, and there were six groups in each determination.

The tissues were incubated, with shaking, for 60 minutes at 37° C in an atmosphere of 5% $CO_2$ — 95% $O_2$ in 1.0 ml of Krebs Ringer bicarbonate buffer containing 11 mM D-glucose, see F. Labrie, cited above. The incubation medium was then replaced by an equal volume of fresh buffer and glucose and the vehicle or test compound was added as indicated in FIG. 1, see below. After a further 20 minutes incubation, 20 $\mu$l of vehicle or prostaglandin $E_2$ ($PGE_2$) in 20 $\mu$l of vehicle were added for the incubation period of four minutes. The vehicle employed for $PGE_2$ and the compounds of formula 1 was: 0.1 ml of sodium carbonate (1.8 mg/ml) and 0.8 ml of water. The concentration of ethanol in the incubation medium containing the test compound was 2%; the final concentration with the additional $PGE_2$-vehicle was 2.2%.

For the assay of the cyclic AMP, the cyclic AMP was extracted from the tissues with 5% trichloroacetic acid and measured by the receptor-binding assay of A. G. Gilman, Proc. Natl. Acad. Sci. U.S.A., 67, 305 (1970). The binding of $^3$H-cyclic AMP to a cyclic AMP-dependent protein kinase forms the basis of the assay. A heat-stable protein, an inhibitor of the cyclic AMP-dependent protein kinase, increases the affinity of the cyclic nucleotide for this enzyme. $^3$H-Cyclic AMP and this inhibitor are present in saturating concentrations of cyclic AMP, and the effect of added unknown or standard cyclic AMP solutions can thus be evaluated from a linear, and nearly theoretical, decrease in the total found $^3$H-cyclic AMP. In the present instance 10 $\mu$g of the protein kinase inhibitor protein, prepared according to Gilman, and 1 $\mu$g of receptor preparation (P-5511, Sigma Chemical Co., the preparation being a cyclic AMP dependent protein kinase from beef heart, see Gilman, cited above) were employed. [8-$^3$H]Cyclic AMP (Schwarz-Mann Co; 28 Ci/mmole) was employed at a final concentration of 40 mM. Unlabeled cyclic AMP was obtained from Calbiochem Co. Assays were performed in triplicate. After filtration, the filters were dried and 10 ml of toluene-phosphor [0.4% 2,5-diphenyloxazole and 0.005% 1,4-bis(5-phenyloxazol-2-yl)-benzene] was employed for scintillation counting. The level of cyclic AMP increased with time and rose to a maximum at about 15 minutes. As the increase of cyclic AMP accumulation was linear with respect to time for at least five minutes, the time period of 4 minutes was employed in subsequent studies, described hereinafter.

Under the above described conditions, the cyclic AMP accumulation increased with the concentration of added $PGE_2$ to a maximum at about 15 $\times$ 10$^{-6}$M $PGE_2$. Linearity was obtained at least to a concentration of 1.5

$\times 10^{-6}$ M; therefore, a concentration of $1.0 \times 10^{-6}$ M was employed in the experiments illustrated by FIG. 1.

When the compounds of formula 1 were examined in the preceding test for their effects on the $PGE_2$-induced cyclic AMP accumulation, 2-(1-hydroxy-2-octynyl)-5-oxocyclopentaneheptanoic acid (see Example 3 hereinafter) and 2-(3-hydroxy-1-octynyl)-5-oxocyclopentaneheptanoic acid (see Example 5) significantly decreased the $PGE_2$-induced accumulation at a concentration of $5 \times 10^{-4}$ M. In contrast, cis-2-(1-hydroxy-2-octenyl)-5-oxocyclopentaneheptanoic acid (see Example 4), an analog of 2-(1-hydroxy-2-octynyl)-5-oxocyclopentaneheptanoic acid in which the triple bond of the latter compound is replaced with a double bond, did not cause an appreciable lowering of the $PGE_2$-induced increase at the same concentration. See FIG. 1.

On the other hand, both the aforementioned compound of formula 1, 2-(1-hydroxy-2-octynyl)- and 2-(3-hydroxy-1-octynyl)-5-oxocyclopentzneheptanoic acid, were ineffective on the basal cyclic AMP accumulation at $5 \times 10^{-4}$ M under similar conditions, while cis-2-(1-hydroxy-2-octenyl)-5-oxocyclopentaneheptanoic acid caused a relatively slight stimulation.

The aforementioned tests show that the above compounds of formula 1 are effective antagonists of the action of the natural prostaglandin $E_2$ to induce cyclic AMP formation in the rat anterior pituitary. In preventing this action of $PGE_2$, the compounds of formula 1 appear to act as pure antagonists since alone they did not exhibit agonist activity.

In FIG. 1.

II = cis-2-(1-hydroxy-2-octenyl)-5-oxocyclopentaneheptanoic acid,

III = 2-(1-hydroxy-2-octynyl)-5-oxocyclopentaneheptanoic acid (1, A = CHOH—C≡C— and $R_1$ = H), and IV = 2-(3-hydroxy-1-octynyl)-5-oxocyclopentaneheptanoic acid (1, A = -C≡C—CHOH— and $R_1$ = H).

The prostanoic acid derivatives of formula 1 are useful pharmacological and therapeutic agents. For a discussion on the application of substances that inhibit the actions of prostaglandins, see K. E. Eakins and J. H. Sanner, in "The Prostaglandins," S. M. M. Karim, Ed., Wiley-Interscience, New York, 1972 pp. 263 - 292, R. J. Flower, Pharmacological Reviews, 26, 33 (1974) and Sanner, cited above.

The compounds of formula 1 can be used in the treatment of complications associated with abnormally increased physiological availability of prostaglandins; for example, habitual abortion, premature labor, diarrhea, nausea, vomiting, cerebral vasospasm, hypotension, fever, bone resorption, sickle cell animia, obstructive lung disease, ulcers, inflammation, hypertriglyceridemia, uveitis and glaucoma. When the compound of formula 1 or a salt thereof is employed for such treatment, it is administered systemically. A preferred mode of administrating the compound is parenteral. In this case it is given in combination with a pharmaceutically acceptable liquid or solid carrier. The compound also can be administered orally in solid form containing such excipients as starch, lactose, sucrose, certain types of clay, and flavoring and coating agents. The proportion of the compound is determined by its solubility in the given carrier, by the given carrier, by the chosen route of administration, and by standard biological practice. For parenteral administration the compound is used in a

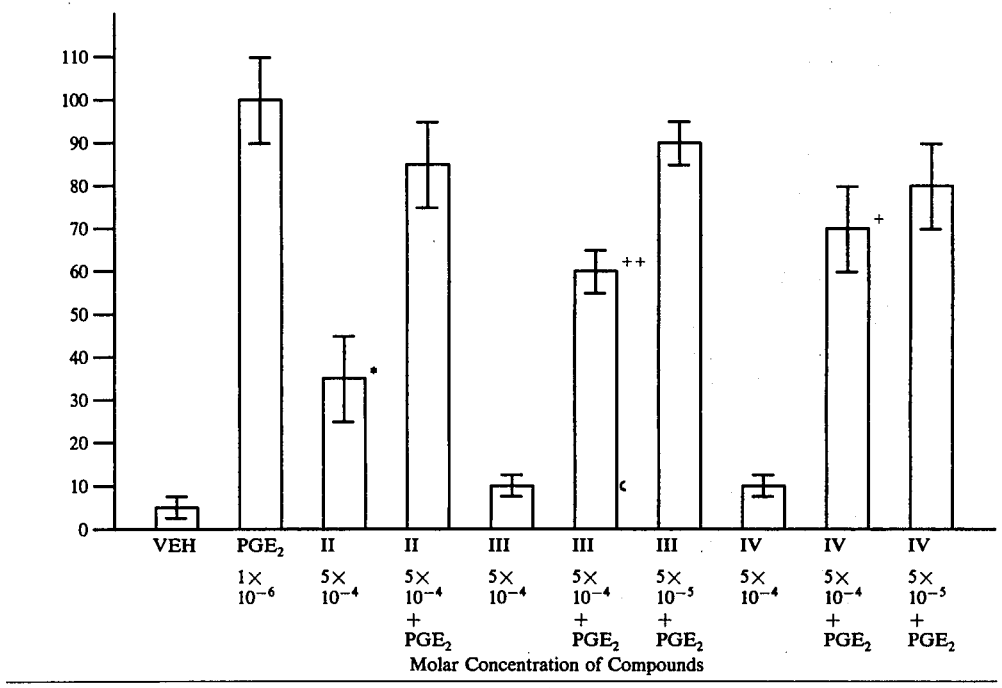

FIG I

Effects of Prostanoic Acid Derivatives on $PGE_2$-Induced Cyclic AMP Accumulation

*P < 0.01 vs vehicle
++P < 0.001,
+ < 0.01 vs $PGE_2$ sterile aqueous solution which may also contain other solutes such as buffers or preservatives, as well as sufficient pharmaceutically acceptable salts of glucose to make the solution isotonic. The dosage will vary with the form of administration and with the particular species of animal to be treated and is preferably kept at a level of from 0.01 to 500 mg per kilogram body weight per day. However, a dosage level in the range of from about 1.0 mg to about 100 mg per kilogram body weight per day is most desirably employed in order to achieve affective results.

For parenteral and oral administration convenient unit dosage forms can range from 5 to 100 mg., or even higher, depending on the subject treated and the particular result desired as will be apparent to those skilled in the art.

The compound of formula 1 may also be administered in one of the long acting, slow-release or depot dosage forms described below, preferably by intramuscular injection or by implantation. Such dosage forms are designed to release from about 0.5 mg to about 50 mg per kilogram body weight per day.

It is often desirable to administer the agent continuously over prolonged periods of time in long-acting, slow-release, or depot dosage forms. Such dosage forms may either contain a pharmaceutically acceptable salt of the agent having a low degree of solubility in body fluids, for example one of those salts described below, or they may contain the agent in the form of a water-soluble salt together with a protective carrier which prevents rapid release. In the latter case, for example, the agent may be formulated with a non-antigenic partially hydrolyzed gelatin in the form of a viscous liquid; or the agent may be absorbed on a pharmaceuticaly acceptable solid carrier, for example, zinc hydroxide, and may be administered in suspension in a pharmaceutically acceptable liquid vehicle; or the agent may be formulated in gels or suspensions with a protective non-antigenic hydrocolloid, for example sodium carboxymethylcellulose, polyvinylpyrrolidone, sodium alginate, gelatine, polygalacturonic acids, for example, pectin, or certain mucopolysaccharides, together with aqueous or non-aqueous pharmaceutically acceptable liquid vehicles, preservatives, or surfactants. Examples of such formulations are found in standard pharmaceutical texts, e.g. in Remington's Pharmaceutical Sciences, 14th Ed., Mack Publishing Co., Easton; Pennsylvania, 1970. Long-acting, slow-release preparations of the agent produced according to the process of this invention may also be obtained by microencapsulation in a pharmaceutically acceptable coating, for example gelatine, polyvinyl alcohol or ethyl cellulose. Further examples of coating materials and of the processes used for microencapsulation are described by J. A. Herbig in "Encyclopedia of Chemical Technology," Vol. 13, 2nd Ed., Wiley, New York 1967, pp 436 - 456. Such formulations, as well as suspensions of salts of the agent which are only sparingly soluble in body fluids, are designed to release from about 10 mg to about 100 mg of the active compound per kilogram body weight per day, and are preferably administered by intramuscular injection. Alternatively, some of the solid dosage forms listed above, for example certain sparingly water-soluble salts or dispersions in or adsorbated on solid carriers of salts of the agent, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

The compound of formula 1 or a salt thereof also may be administered topically or intradermally in the form of 0.1 to 5% solution with pharmaceutically acceptable excipients. The frequency of instillation varies with the subject under treatment; for example, in the case of glaucoma topical administration generally varies from one to five drops daily applied to the eyes.

Process

With regard to the process for preparing the compound of formula 1 in which A is —CHOH—C≡C—, a preferred embodiment is described as follows.

The transformation of the starting material of formula 2 in which $R^1$ is hydrogen or lower alkyl and $R^2$ is a hydroxy protective group to the corresponding dihydroxyprostanoic acid derivative of formula 3 is performed conveniently by bringing the starting material of formula 2 into contact with the lithium derivative of 1-heptyne in an aprotic solvent, preferably the solvent in which the lithium derivative is prepared, for example, toluene, hexane or tetrahydrofuran. Times and temperatures for this reaction are variable. Generally a reaction time of one to 24 hours a temperature range of from −80° to 0° C is employed. Preferably the lithium derivative of 1-heptyne in hexane or toluene is added to a solution of the starting material of formula 2 in hexane or toluene at −70° to −78° C (acetone - dry ice bath temperature). The reaction mixture is stirred at the low temperature for one to four hours and then allowed to warm to room temperature. The product of formula 3 thereafter is isolated readily by the usual extraction procedures.

The starting material of formula 2 in which $R^1$ is lower alkyl is readily prepared according to the method of J. Bagli and T. Bogri, Tetrahedron Letters, 3815 (1972) for the preparation of 2-formyl-5-(tetrahydropyran-2-yloxy)-cyclopentaneheptanoic acid methyl ester (2; $R^1$=CH$_3$ and and $R^2$ = tetrahydropyran-2-yl) with the appropriate variation with respect to $R^1$ and $R^2$. See also U.S. Pat. No. 3,773,795, issued Nov. 20, 1973. The starting materials of formula 2 in which $R^1$ is hydrogen are obtained from their corresponding lower alkyl esters, noted above, by hydrolysis; for instance, see Example 1.

The dihydroxyprostanoic acid derivative of formula 3 in which $R^1$ is hydrogen or lower alkyl and $R^2$ is a hydroxy protective group and $R^3$ is hydrogen, obtained as described above, is transformed readily to its corresponding acyl derivative of formula 3 in which $R^3$ is lower alkanoyl by reaction with a lower alkanoic anhydride or lower alkanoic acid chloride, preferably acetic anhydride or acetyl chloride, in the presence of a proton acceptor, preferably pyridine, whereby the side chain hydroxyl is acylated.

The latter acyl derivative of formula 3 then is subjected to conditions which do not affect the lower alkanoyl group but are known to be effective for removal of the hydroxy protective groups. Convenient conditions include dissolving the acyl derivative 3 in 25 to 50% aqueous acetic acid and allowing the solution to stand for one to eight hours at 20° to 60° C.

In this manner the hydroxyl on the ring of the compound of formula 3 is deprotected to give the corresponding hydroxy compound of formula 3 in which $R^1$ is hydrogen or lower alkyl, $R^2$ is hydrogen and $R^3$ is lower alkanoyl. The latter compound now is oxidized with a suitable oxidizing agent to give the corresponding ketone of formula 4 in which $R^1$ is hydrogen or lower alkyl and $R^3$ is lower alkanoyl. Suitable oxidizing agents include chromium trioxide-pyridine complex and aqueous chromium trioxide-sulfuric acid in acetone, see K. Bowden, et al., J. Chem. Soc., 36 (1946) and L. F. Fieser and M. Fieser in "Reagents for Organic Synthesis", John Wiley and Sons, Inc., New York, London and Sydney, 1967, pp 142 – 147.

Subsequent hydrolysis of the above compound of formula 4 by a suitable base, for example, sodium or potassium hydroxide, in the presence of water and a cosolvent, for example a lower alkanol such as methanol or ethanol, at 20° to 50° C for two to 24 hours removes the alkanoyl group and ester group, if present, to give the corresponding compound of formula 1 in which A is —CHOH—C≡C— and $R^1$ is hydrogen.

If desired the preceding compound of formula 1 in which $R^1$ is hydrogen is transformed into the corresponding compound of formula 1 in which $R^1$ is lower alkyl by esterification with a lower alkanol containing on the three carbon atoms, for example, methanol, ethanol or propanol, in the presence of an acid, for instance, sulfuric acid, hydrochloric acid or preferably perchloric acid. Optionally, this esterification is effected by treating the compound of formula 1 in which $R^1$ is hydrogen with an appropriate diazoalkane, for example, diazomethane or diazoethane.

A preferred embodiment for preparing the compound of formula 1 in which A is —C≡C—CHOH— entails reacting the ketoacid of formula 5 ($R^1 = H$) or a lower alkyl ester thereof (5, $R^1 = $ lower alkyl), preferably tne methyl ester, with an alane derivative of the compound of formula HC≡CH(OR$^4$)—(CH$_2$)$_4$—CH$_3$ in which $R^4$ is a hydroxy protective group, preferably THP, to obtain the corresponding compound of formula 6. The alane derivative is generated in situ for the corresponding lithium derivative, in the presence of aluminum chloride, for example see R. Pappo and P. W. Collins, Tetrahedron Letters, 2627 (1972) and J. Fried, et al., Tetrahedron Letters, 1379 (1969). Convenient reaction conditions for this reaction are the same as described hereinbefore for the transformation of the compound of formula 2 to the compound of formul 3.

The requisite ketoacid of formula 5 and its lower alkyl esters are known or are readily prepared by applying the procedures described by J. Bagli and T. Bogri, Tetrahedron Letters, 3815 (1972) and U.S. Pat. No. 3,773,795, issued November 20, 1973.

The requisite lithium derivative of the acetylenic compound of formula HC≡C(OR$^4$)—(CH$_2$)$_4$—CH$_3$ is obtained by reacting the acetylenic compound with a lower alkyl lithium derivative, for example, propyl lithium, t-butyl lithium and hexyl lithium in an aprotic solvent, for example, hexane or toluene. Convenient times and temperature for the formation of this derivative include temperatures ranging from −80° – 0° C and times of 10 minutes to two hours. The acetylenic compound is prepared by introducing a hydroxy protecting group on the free hydroxyl of commercially available 1-octyn-3-ol.

Returning now to the compound of formula 6 in which $R^1$ is hydrogen or lower alkyl and $R^4$ is a hydroxy protective group, prepared as described above, the compound is transormed to the corresponding compound of formula 1 in which A is —C≡C—CHOH— and $R^1$ is hydrogen or lower alkyl under conditions known to be effective for removing hydroxy protective groups as described hereinbefore. Furthermore, and if desired, the latter compound of formula 1 in which $R^1$ is lower alkyl is hydrolyzed by a suitable base, for example sodium or potassium hydroxide, in the presence of water and a cosolvent, for example, a lower alkanol such as methanol or ethanol, at 20° to 50° C for two to 24 hours to give the desired compound of formula 1 in which A is —C≡C—CHOH— and $R^1$ is hydrogen.

The following examples illustrate further this invention.

EXAMPLE 1

2-Formyl-5-(tetrahydropyran-2-yloxy)-cyclopentaneheptanoic acid (2, $R^1 = H$ and $R^2 = $ tetrahydropyran-2-yl)

To a solution of 2-formyl-5-(tetrahydropyran-2-yloxy)-cyclopentaneheptanoic acid methyl ester (23.64 g), described by J. Bagli and T. Bogri, Tetrahedron Letters, 3815 (1972), see also U.S. Pat. No. 3,773,795 issued November 20, 1973, in methanol (20 ml) is added 10% NaOH (33.5 ml). The reaction mixture is stirred under a nitrogen atmosphere at 40° C (bath temperature) for 18 hr. The mixture is cooled and the methanol is evaporated from the mixture. The residue is taken up in ether and the resulting mixture is washed with a small amount of water. The aqueous layer is acidified with acetic acid and extracted with ether. The ether extract is washed with water, dried and concentrated to yield the title compound, $\nu_{max}^{film}$ 2700, 1712, 1125 and 1025 cm$^{-1}$.

EXAMPLE 2

2-(1-Hydroxy-2-octynyl)-5-(tetrahydropyran-2-yloxy)-cyclopentaneheptanoic Acid (3: $R^1 = H$, $R^2 = $ tetrahydropyran-2-yl and $R^3 = H$)

Under a nitrogen atmosphere at −40° C, a solution of 70.4 ml of n-butyl lithium in hexane (2.3 molar) is added dropwise to a solution of 1-heptane (14.78 g, 2.2 equivalents) in 50 ml of toluene. The mixture is stirred at the same temperature for 10 minutes. The solution is transferred carefully to an additional funnel and added at to a solution of 2-formyl-5-(tetrahydropyran-2-yloxy)-cyclopentaneheptanoic acid (22.82 g, 1 equivalent), described in Example 1, in 50 ml of toluene cooled to −70° C. The reaction is stirred at the same temperature for 2 hr. The mixture then is diluted with ether and washed with water. The aqueous layer is acidified with acetic acid and extracted with ether. The ether extract is washed with water, dried and concentrated to give the title compound, nmr (CDCl$_3$) δ 0.89 (t, 3H), 3.90 (broad, 1H), 4.33 (m, 1H).

In the same manner but replacing 2-formyl-5-(tetrahydropyran-2-yloxy)-cyclopentanoic acid with an equivalent amount of its corresponding methyl, ethyl or propyl ester, the corresponding methyl, ethyl and propyl esters of the title compound are obtained, respectively.

A sample of the title compound is esterified with diazomethane to give the corresponding methyl ester, $\nu_{max}^{film}$ 3400, 1730, 1025 cm$^{-1}$.

EXAMPLE 3

2-(1-Hydroxy-2-octynyl)-5-oxocyclopentaneheptanoic Acid (1; A = —CHOH—C≡C— and $R^1 = H$)

To a solution of 2-(1-hydroxy-2-octynyl)-5-(tetrahydropyran-2-yloxy)-cyclopentaneheptanoic acid (11.5 g), described in Example 2, in dry pyridine (50 ml), acetic anhydride (35.6 ml) is added. The mixture is stirred overnight. The solvent is removed under reduced pressure. The residue is dissolved in ether and the solution is washed with ether, dried and concentrated to yield 2-(1-acetoxy-2-octynyl)-5-(tetrahydropyran-2-yloxy)-cyclopentaneheptanoic acid, (3; $R^1 = H$, $R^2 =$ tetrahydropyran-2-yl and $R^3 = CH_3CO$), $\nu_{max}^{film}$ 1700, 1735 cm$^{-1}$.

The latter acetate (11.25 g) is dissolved in acetic acid (108 ml) and water (54 ml). The mixture is stirred at 55° C for 2.5 hr. The acetic acid is removed. The residue is dissolved in ether. The solution is washed with water, dried and concentrated to give 2-(1-acetoxy-2-octynyl)-5-hydroxy-cyclopentaneheptanoic acid (3; $R^1$ and $R^2 = H$ and $R^3 = CH_3CO$), $\nu_{max}^{film}$ 3350, 1700, 1730 cm$^{-1}$.

The latter compound (11.4 g) in acetone (128 ml) is cooled to −20° C. The cooled solution is treated dropwise with a solution of chromic anhydride and sulfuric acid in water (Jones' Reagent). The mixture is stirred at 0°-10° C for 1 hr., treated with 2 ml of methanol and stirred for an additional hour. The solvent is evaporated. The residue is taken up in ether. The ether phase is washed with water, dried and concentrated to yield 2-(1-acetoxy-2-octynyl)-5-oxocyclopentaneheptanoic acid (4; $R^1 = H$ and $R^3 = CH_3CO$). The infrared spectrum of the latter compound showed a new band in the carbonyl region ($\nu_{max}^{CHCl_3}$ 1725 cm$^{-1}$) and the absence of hydroxyl absorption.

The latter compound (9.12 g) is dissolved in methanol (133 ml) and sodium hydroxide (10%, 19 ml). The mixture is stirred 18 hr. The solvent is removed under reduced pressure. The neutral fraction is separated and the aqueous layer is acidified and extracted with ether. The ether phase is washed, dried and concentrated. The residue is purified by chromatography on silica gel to give the title compound, $\nu_{max}^{CHCl_3}$ 3500, 2220, 1725, 1700 cm$^{-1}$, nmr (CDCl$_3$) δ 0.87 (t, 3H), 4.53 (m, 1H). Chromatographic examination (thin layer chromatography on silica gel plates) indicates that this product is a mixture of the two possible isomeric alcohols each having very similar chromatographic behavior.

In the same manner but replacing 2-(1-hydroxy-2-octynyl)-5-(tetrahydropyran-2-yloxy)-cyclopentaneheptanoic acid with an equivalent amount of its corresponding methyl, ethyl or propyl ester, the corresponding methyl, ethyl and propyl esters of the compound of formula 4 are obtained, respectively. Hydrolysis of the latter esters with 10% sodium hyroxide in the manner described above gives the title compound.

EXAMPLE 4 cis-2-(1-Hydroxy-2-octenyl)-5-oxocyclopentaneheptanoic Acid

A solution of 2-(1-hydroxy-2-octynyl)-5-oxocyclopentaneheptanoic acid (1.12 g), described in Example 3, in 20 ml of ethyl acetate is subjected to hydrogenation with Lindlar catalyst (200 mg) to yield the title compound which is purified by chromatography on silica gel. [Lindlar catalyst is a mixture of palladium and lead oxide on calcium carbonate, H. Lindlar, Helv. Chim. Acta, 35, 446 (1952)]. The title compound has $\nu_{max}^{film}$ (broad OH absorption) 1730, 1710 cm$^{-1}$; nmr (CDCl$_3$) δ 5.54 (m, 2H), 7.14 (broad, 2H).

EXAMPLE 5

2-(3-Hydroxy-1-octynyl)-5-oxocyclopentaneheptanoic acid (1; A = —C≡C—CHOH— and $R^1 = H$)

Under a nitrogen atmosphere at −25° C, a solution of butyl lithium (50 ml of 2.2 molar solution in hexane) is added to a solution of 3-(tetrahydropyran-2-yloxy)-1-octyne {21.0 g, readily prepared from 1-octyn-3-ol (E. Crundwell, et al., J. Med. Chem., 8, 41 (1965)) and dihydropyran in the presence of conc. HCl} in toluene (25 ml). The mixture is stirred for 15 minutes and aluminum chloride (4.46 g) is added. After the reaction mixture has been stirred for an additional 45 minutes at −20° C, 5-oxo-1-cyclopentane-1-heptanoic acid methyl ester (11.2 g), described by J. Bagli and T. Bogri, Tetrahedron Letters, 3815 (1972) and U.S. Pat. No. 3,773,795, issued November 20, 1973, is added and the resultant mixture is allowed to come to room temperature (20°-25° C). The mixture is stirred for 16 hr. then diluted with saturated NH$_4$Cl and extracted with ether. The ether extract is washed with saturated NH$_4$Cl, water, dried and concentrated to yield an oily residue. Chromatography of the residue on silica gel using ethyl acetate-benzene (1:9) as eluant affords 2-[3-(tetrahydropyran-2-yloxy)-1-octynyl]-5-oxocyclopentaneheptanoic acid methyl ester (6; $R^1 = CH_3$ and $R^4 =$ tetrahydropyran-2-yl).

A solution of the latter compound (4.98 g) and p-toluenesulfonic acid (0.35 g) in methanol-water (9:1) (50 ml) is stirred at 20°-25° C for 1 hr. The solvent is removed under reduced pressure. The residue is taken up in ether. The ether solution is washed with water, dried and concentrated. The residue is subjected to chromatography on silica gel using ethyl acetate-benzene (1:9) as eluent. Concentration of the eluate gives 2-(3-hydroxy-1-octynyl)-5-oxocyclopentaneheptanoic acid methyl ester (1; A = —C≡C—CHOH— and $R^1 = CH_3$), $\nu_{max}^{film}$ 3420, 1730, 1700 cm$^{-1}$.

A solution of the latter compound (0.97 g) in methanol (6 m) is mixed with 5% aqueous NaOH (3.3 ml). The mixture is stirred at 20°-25° C for 18 hr. The mixture is partitioned between ether and water to separate it into basic, neutral and acidic fractions. Isolation of the acid fraction, followed by chromatography of the latter fraction on silica gel using ethyl acetate: hexane: methanol (5:5:0.1) yields the title compound, $\nu_{max}^{film}$ (broad hydroxyl absorption), 1725, 1700 cm$^{-1}$, nmr (CDCl$_3$) δ 0.90 (t, 3H), 4.50 (m, 1H), 6.89 (broad singlet).

Chromatographic examination (thin layer chromatography on silica gel) indicates that this product is a mixture of the two isomeric alcohols, each having very similar chromatographic behavior.

In the same manner but replacing 5-oxo-1-cyclopentene-1-heptanoic acid methyl ester with an equivalent amount of 5-oxo-1-cyclopentene-1-heptanoic acid ethyl or propyl ester, see U.S. Pat. No. 3,773,795, the corresponding ethyl and propyl esters of 2-(3-hydroxy-1-octynyl)-5-oxocyclopentaneheptanoic acid are obtained, respectively, instead of 2-(3-hydroxy-1-octynyl)-5-oxocyclopentaneheptanoic acid methyl ester, noted above.

We claim:
1. A compound of the formula

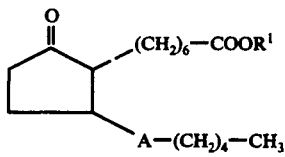

in which A is —CHOH—C≡C— and $R^1$ is hydrogen or lower alkyl.

2. 2-(1-Hydroxy-2-octynyl)-5-oxocyclopentaneheptanoic acid, as claimed in claim 1.

3. A pharmaceutical composition for relieving a complication arising from abnormally increased physiological availability of prostaglandins in a host, comprising an effective amount of: a compound of formula 1

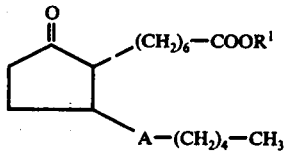

in which A is —CHOH—C≡C— and $R^1$ is hydrogen or lower alkyl, and a pharmaceutically acceptable carrier.

4. The pharmaceutical composition of claim 3 in which the compound of formula 1 is 2-(1-hydroxy-2-octynyl)-5-oxocyclopentaneheptanoic acid.

5. The pharmaceutical composition of claim 3 in which the compound of formula 1 is present in a unit dose of from 5 to 100 mg.

* * * * *